(12) United States Patent
van der Maas (10) Patent No.: US 6,918,952 B2
(45) Date of Patent: Jul. 19, 2005

(54) QUICK-CHANGE FILTER SYSTEM AND A BASE AND A QUICK-CHANGE FILTER INTENDED FOR SUCH A SYSTEM

(75) Inventor: Marinus Frans van der Maas, Arnemuiden (NL)

(73) Assignee: SGT Singapore Holdings Pte Ltd., Singapore (SG)

( * ) Notice: Subject to any disclaimer, the term of this patent is extended or adjusted under 35 U.S.C. 154(b) by 0 days.

(21) Appl. No.: 10/449,817

(22) Filed: May 30, 2003

(65) Prior Publication Data

US 2004/0231517 A1 Nov. 25, 2004

(30) Foreign Application Priority Data

May 23, 2003 (NL) ............................................. 1023520

(51) Int. Cl.⁷ ......................... B01D 53/04; B01D 27/10; B01D 46/42
(52) U.S. Cl. .......................... 96/117.5; 96/136; 96/147; 96/416; 55/312; 55/314; 210/234; 210/443
(58) Field of Search ........................ 96/117.5, 134–136, 96/147, 153, 154, 416, 417, 420; 55/309, 312, 314, 350.1; 210/234, 235, 238, 443, 444

(56) References Cited

U.S. PATENT DOCUMENTS

| | | | | |
|---|---|---|---|---|
| 3,330,098 A | * | 7/1967 | Delin | 96/151 |
| 3,819,052 A | * | 6/1974 | Firth | 210/90 |
| 3,841,484 A | * | 10/1974 | Domnick | 210/95 |
| 3,909,221 A | * | 9/1975 | Bengtsson | 55/314 |
| 4,345,923 A | * | 8/1982 | Schoen | 96/139 |
| 4,529,514 A | * | 7/1985 | Gruett | 210/234 |
| 4,904,382 A | | 2/1990 | Thomsen | |
| 5,478,378 A | * | 12/1995 | van der Maas et al. | 96/106 |
| 5,558,688 A | * | 9/1996 | Cowan et al. | 55/312 |
| 5,591,332 A | * | 1/1997 | Reid et al. | 210/235 |
| 5,645,720 A | * | 7/1997 | Godines | 210/282 |
| 5,674,381 A | * | 10/1997 | Den Dekker | 210/85 |
| 5,695,168 A | * | 12/1997 | Williams | 251/149.4 |
| 5,698,093 A | * | 12/1997 | Pyle et al. | 210/136 |
| 5,925,245 A | * | 7/1999 | Bradford et al. | 210/232 |
| 6,027,644 A | * | 2/2000 | Magnusson et al. | 210/235 |
| 6,149,718 A | | 11/2000 | Cowan et al. | |
| 6,458,269 B1 | * | 10/2002 | Bassett et al. | 210/119 |
| 6,551,503 B2 | * | 4/2003 | Neirs et al. | 210/85 |
| 6,565,745 B2 | | 5/2003 | Hodgin et al. | |
| 2003/0025598 A1 | | 2/2003 | Wolf et al. | |
| 2003/0127384 A1 | * | 7/2003 | Kapur | 210/235 |
| 2003/0168389 A1 | * | 9/2003 | Astle et al. | 210/85 |

FOREIGN PATENT DOCUMENTS

| | | |
|---|---|---|
| DE | 202 17 595 | 4/2003 |
| DE | 101 51 269 | 5/2003 |
| EP | 0 606 960 | 2/1997 |
| JP | 2001-478327 | 6/2001 |
| WO | WO 01/17654 | 3/2001 |
| WO | WO 01/95993 | 12/2001 |

* cited by examiner

Primary Examiner—Robert H. Spitzer
(74) Attorney, Agent, or Firm—Weingarten, Schurgin, Gagnebin & Lebovici LLP (57) ABSTRACT

A quick-change filter system provided with at least one base and at least one quick-change filter, which base is provided with a filter coupling provided with a gas inlet stub for connection to an inlet of the filter and with a gas outlet stub for connection to an outlet of the filter, the filter being provided with a housing, which is at least partly filled with filter material and to which the inlet and the outlet are connected, and with a quick-change coupling arranged for cooperation with the filter coupling of the base, the coupling containing the inlet and the outlet of the filter, the base being provided with a mechanism for manually connecting the filter to the base, and being provided with a sealing mechanism for automatic, gastight sealing of the gas outlet stub and the gas inlet stub when decoupling the filter from the base.

28 Claims, 8 Drawing Sheets

QUICK-CHANGE FILTER SYSTEM AND A BASE AND A QUICK-CHANGE FILTER INTENDED FOR SUCH A SYSTEM

The invention relates to a quick-change filter system that is provided with at least one base and at least one quick-change filter which can be placed on such a base.

A quick-change filter intended for such a system is known from EP-A-0 606 960 of applicant. In addition, applicant puts such quick-change filter systems into circulation. In practice, the quick-change filter is called a cartridge.

An object of the invention is a new quick-change filter system that is provided with a quick-change filter in which no backflow of gas takes place in the filter housing thereof.

Another object of the invention is a new quick-change filter system that is provided with a quick-change filter that is arranged for filtering hydrocarbon compounds from a gas to be led through the quick-change filter and in which system it can be observed whether the filter is already saturated.

A next object of the invention is to provide a quick-change filter system that has a higher capacity and, in addition, an improved cleaning effect.

A further object of the invention is to provide a filter system of which the status can be determined automatically.

Another further object of the invention is to provide a quick-change filter system in which the detachment of the filter from the base does not lead to the shutting off of the gas flow.

A next object of the invention is to prevent that inferior filters are mountable on the base of the quick-change filter system according to the invention.

Another next object of the invention is to provide a solid connection between the base and a quick-change filter, precluding the possibility that the quick-change filter is connected wrongly to the base.

Another object of the invention is to provide a quick-change filter system that is provided with a quick-change filter arranged for filtering water and oxygen from a gas to be led through the quick-change filter and in which system it can be observed whether the filter is already saturated Yet another object of the invention is to provide a quick-change filter system that is provided with a quick-change filter that can be used directly, that is, without pre-flushing, at least after a minimal pre-flushing time. As for the known filters, the filter usually needs to be flushed for some time with the carrier gas before the carrier gas from the filter can be used for processes. An object of the invention is a quick-change filter system of which the flushing time can be reduced or even omitted.

For this purpose, the invention provides a quick-change filter system provided with at least one base and at least one quick-change filter, which base is provided with an inlet connecting element and an outlet connecting element for connecting the base to a fluid pipe system, the base being provided with a filter coupling part provided with a gas inlet stub for connection to an inlet of the quick-change filter and with a gas outlet stub for connection to an outlet of the quick-change filter, the quick-change filter being provided with a filter housing, which is at least partly filled with filter material and to which the inlet and the outlet are connected, and with a quick-change coupling arranged for cooperation with the filter coupling part of the base, the quick-change coupling containing the inlet and the outlet of the quick-change filter, the base being provided with means for manually connecting the quick-change filter to the base, and being provided with sealing means for the automatic, gastight sealing of the gas outlet stub and the gas inlet stub when decoupling the quick-change filter from the base.

To prevent backflow in the filter housing, the flow resistance of the gas inlet stub can be larger than the flow resistance of the gas outlet stub, such that backflow of gas in the filter housing is prevented.

For the purpose of observation of the saturation of the filter material of a quick-change filter that removes hydrocarbons from a carrier gas, the filter housing can be manufactured from glass, so that it is transparent, with the housing containing, in addition to the filter material, an indicator that changes color when the filter material is saturated or at least loses its filtering effect, with the filter material removing hydrocarbons from the gas, with the indicator changing color when it comes into contact with hydrocarbons. For this purpose, the indicator can contain potassium dichromate and the filter material active carbon. In addition to potassium dichromate, the indicator can also contain silica gel and sulphuric acid.

To obtain a larger filter capacity, in the quick-change filter system, two quick-change filters of the same type can be connected in parallel in the pipe system. Surprisingly, in addition to the larger capacity, that is, standing time, this also yields a considerably better cleaning of the gas. It is suspected that this is the result of the fact that the rate of gas flow in two filters connected in parallel is considerably lower and that thus the residence time of the gas in the filter material is considerably longer. This longer residence time is suspected to lead to the considerably better cleaning of the gas. Optionally, such a parallel coupling can be simply realized using a base provided with at least one pair of filter coupling parts, with the inlet connecting element connecting to an inlet channel in the base, with the outlet connecting element connecting to an outlet channel in the base, with the gas inlet stubs of a pair of filter coupling parts each being connected to the inlet channel, with the gas outlet stubs of a pair of filter coupling parts each being connected to the outlet channel.

To be able to simply retrieve the data of the various quick-change filters in a quick-change filter system, in each quick-change filter thereof a transponder can be incorporated. The transponders can be read out from a distance. In this manner, it can be simply determined how long a specific filter is already in use and whether it needs to be replaced. When the evaluation of these data in a control also takes into account the amount of gas flowed through, the use of indicators in the filters can be even dispensed with. In fact, by monitoring the remaining life, the system can warn the user when the filter needs to be replaced. For reading out the transponder, for instance one of the bases, some bases or each base of the quick-change filter system can be provided with a receiver for reading out a transponder of a quick-change filter.

Optionally, the base is provided with a by-pass pipe and means for creating a fluid connection, via the by-pass pipe, between the inlet connecting element and the outlet connecting element when a quick-change filter is decoupled from the base and for closing off this fluid connection when a quick-change filter is placed on the base.

Such a by-pass pipe minimizes the chance of air from the environment diffusing into the pipe system when the quick-change filter is detached from the base. As for the known base, the gas flow was shut off when the quick-change filter was removed. In this embodiment, unfiltered gas is led through instead. There are process conditions in which such a solution produces better results. In any case, the process is not interrupted in this solution, although very temporarily, unfiltered gas is used.

To prevent that filters of other manufacturers are placed on a base of applicant, the filter coupling part of the base and the quick coupling of the quick-change filter can be provided with mutually cooperating form features, which ensure that only quick-change filters intended for the base in question can be placed on the base.

Such a measure is highly important because when quick-change filters from other manufacturers than the manufacturer of the base are placed, the effect of the quick-change filter system can no longer be guaranteed. Examples of various form features are described in the claims.

For the purpose of filtering water vapor and oxygen from the gas, the filter housing can be at least partly filled with a filter material that is put into circulation under the brand name nanochem®. The firm of Matheson-Trigas puts this material into circulation. This filter material can also serve as an indicator because it already shows a coloring when it comes into contact with a gas that contains a few ppb of oxygen or water. When the filter material nanochem® is also used as an indicator, the filter housing naturally needs to be manufactured from glass.

For the purpose of minimizing the time the user needs to pre-flush a new quick-change filter, the quick-change filter from the system can already be pre-flushed in the factory, using the gas that it is intended to clean later, with, after pre-flushing, the filter housing being sealed such that hardly any air or gases from the air diffuse into the filter or flushing gas diffuses out of the filter. This saves the end user a considerable amount of time, so that he can use his gas chromatograph, mass spectrograph or LCMS sooner after changing a quick-change filter. The filter is then a gas-specific filter.

In particular when the filter has already been pre-flushed with helium in the factory, the construction and the sealing of the filter housing need to meet stringent requirements. In fact, helium will easily diffuse through, for instance, a plastic housing or a faulty sealing.

The invention also relates to a quick-change filter that is evidently intended for a quick-change filter system according to the invention.

The invention further relates to a base that is evidently intended for a quick-change filter system according to the invention.

Further elaborations of the invention are described in the subclaims and will be clarified below on the basis of two exemplary embodiments, with reference to the drawing, in which:

In the various figures, like parts will be numbered alike.

Figure 1:
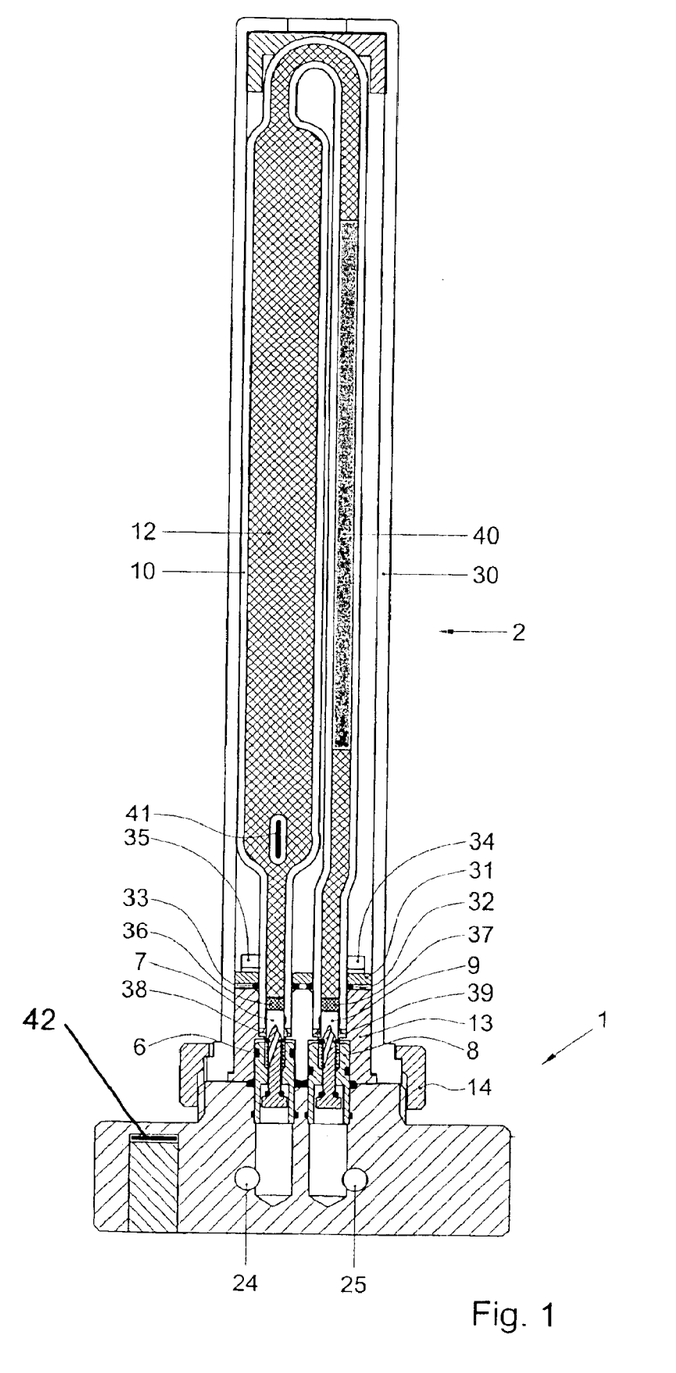
FIG. 1 shows a cross-sectional view of a base with a quick-change filter placed thereon.

FIG. 1 shows, in cross-sectional view, a combination of a base 1 with a quick-change filter 2 placed thereon, which combination can be part of a quick-change filter system in which one or more of such combinations are present.

As FIGS. 1–6 show, the base is generally provided with an inlet connecting element 3 and an outlet connecting element 4 for connecting the base to a fluid pipe system. An inlet channel 24 opens into the inlet connecting element 3. An outlet channel 25 opens into the outlet connecting element 4. The base 1 is further provided with at least one filter coupling part 5 provided with a gas inlet stub 6 for connection to an inlet 7 of the quick-change filter 2 and with a gas outlet stub 8 for connection to an outlet 9 of the quick-change filter 2.

The base 1 is provided with means for manually connecting the quick-change filter 2 to the base 1. In the present embodiment, this is a screw ring 14 that can be screwed onto the filter coupling part 5 provided with screw thread 15 while clamping the bottom side of the quick-change filter 2. The fixing can thus be done manually, which means that no tools need to be used.

Figure 2:
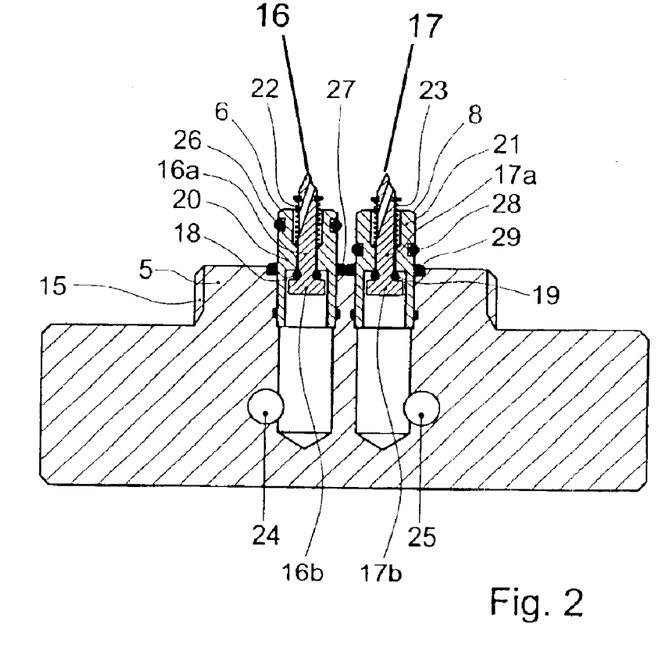
FIG. 2 shows a similar cross-sectional view of a base without a quick-change filter.
Figure 3:
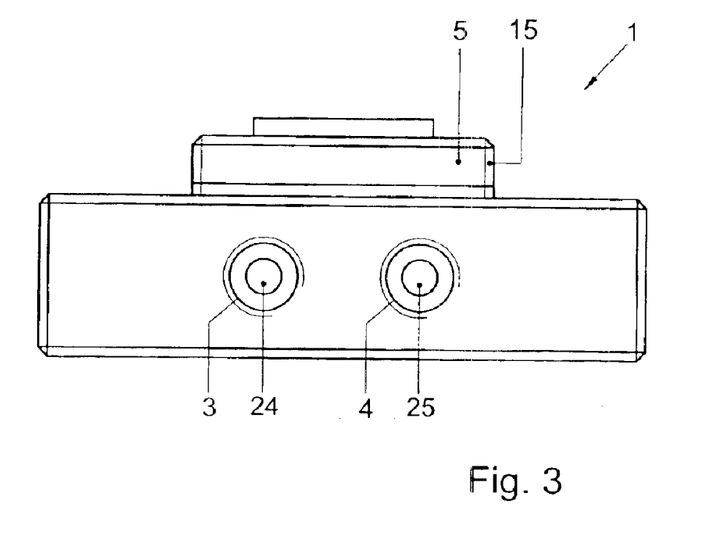
FIG. 3 shows a back view of the base.
Figure 4:
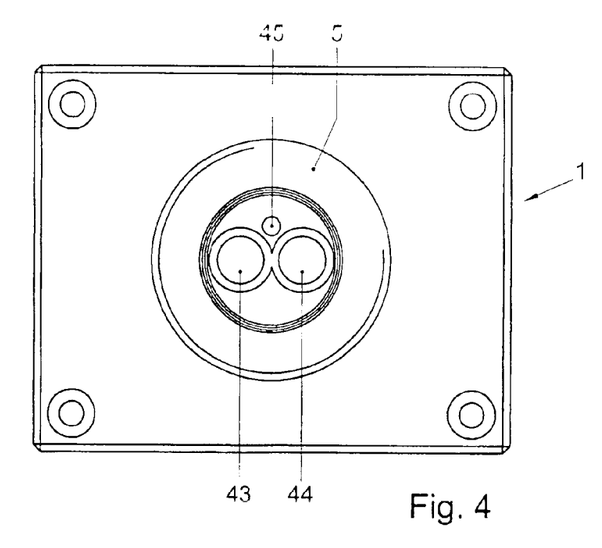
FIG. 4 shows a top view of the base shown in FIG. 3.
Figure 5:
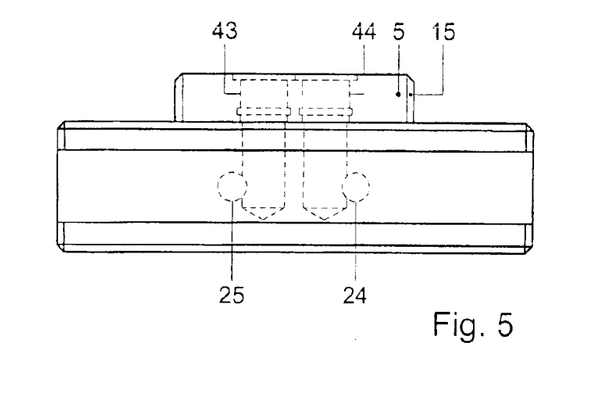
FIG. 5 shows a front view of the base shown in FIGS. 2–4.
Figure 6:
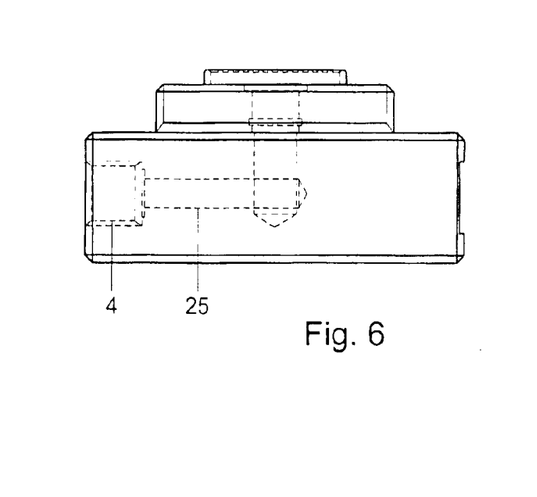
FIG. 6 shows a side view of the base shown in FIGS. 2–5.

As is clearly visible in FIG. 2, the base 1 is provided with sealing means for automatic, gastight sealing of the gas outlet stub 8 and the gas inlet stub 6 when decoupling the quick-change filter 2 from the base 1. The sealing means comprise a valve 16 in the inlet stub 6 and a valve 17 in the outlet stub 8. Each valve 16, 17 is provided with a valve flange 16a, 17a and a valve stem 16b, 17b. On the valve flange 16a, 17a rests a sealing ring 18, 19, which in a closed position of the valve is pressed against a valve seat 20, 21 in the inlet and outlet stub 6, 8 respectively. The valves 16, 17 are each kept in a closed position by a spring 22, 23 that is under prestress (see FIG. 2). By placing a quick-change filter 2 on the base 1, the valves 16, 17 are opened automatically against the effect of the springs 22, 23 (see FIG. 1). In this manner, a fluid connection is created between the inlet connecting element 3 and the inlet 7 of the filter 2 via inlet channel 24 and between the outlet connecting element 4 and the outlet 9 of the filter 2 via outlet channel 25. It is also clearly visible in FIG. 2 that on the gas inlet stub 6 and the gas outlet stub 8 two sealing rings 26, 27 and 28, 29 respectively are provided to create a gastight sealing. FIGS. 3–6 show some views of the base 1 in which the gas inlet stub 6 and the gas outlet stub 8 have been omitted. The stubs 6 and 8 are placed in the openings 43, 44 in the base (see FIGS. 4 and 5). FIG. 4 further shows an opening 45 in which a dowel pin will be placed that serves to prevent that a quick-change filter 2 is wrongly connected to the base. The presence of the dowel pin and the corresponding opening in the quick-change coupling 13 of the quick-change filter 2 ensures that the filter 2 is always connected to the base 1 in the right manner.

The quick-change filter 2 is provided with a filter housing 10 with an inlet 7 and an outlet 9. The filter housing 10 is at least partly filled with filter material 12. The quick-change filter 2 also has a quick-change coupling 13 arranged for cooperation with the filter coupling part 5 of the base 1. The quick-change coupling 13 contains the inlet 7 and the outlet 9 of the quick-change filter 2. The filter housing 10 is surrounded by a protective cap 30. Such a protective cap 30 prevents the filter housing 10 from breaking as a result of bumping. In addition, the protective cap 30 protects the user when the filter housing 10 would explode as a result of the overpressure therein. The connection between the filter housing 10, which in the present exemplary embodiment is designed in glass, and the quick-change coupling 13 is created by means of a clamping plate 31 and two O-rings 32, 33. By clamping the clamping plate 31 using bolts 34, 35, the O-rings 32, 33 are deformed and thus clamp the ends of the filter housing 10. The filter material 12 is kept in place by two gas-permeable plugs 36, 37. In the inlet 7 and the outlet 9, caps 38, 39 are placed which are bored by the valve stems 16b, 17b when placing a filter 2 on the base 1.

What is special about the exemplary embodiment shown is that this is a quick-change filter 2 intended for removing hydrocarbons from a gas, while the presence of an indicator 40 also makes it visible when the filter material 12 is saturated. In the present exemplary embodiment, the filter material 12 comprises active carbon and the indicator contains potassium dichromate that changes color when it comes into contact with hydrocarbons. In another embodiment, the filter material, a part of the filter material and/or the indicator is nanochem® which is put into circulation by Matheson-Trigas.

What is also special about the exemplary embodiment shown in FIG. 1 is that the quick-change filter 2 is provided with a transponder 41. The base 1 is provided with a receiver 42. The advantages of such provisions are that the status of the various filters 2 in a quick-change filter system can be determined automatically. In fact, when the receivers 42 are connected to a central processing unit, the period of use and optionally the remaining standing time of the various filters can simply be monitored. Thus, the system can warn the user that new filters need to be ordered or the system can even place the order automatically before the end of the life of the filter is reached The transponder 41 and the receiver 42 can also be used to check whether the right filter is placed on the base 1. Optionally, the transponder 41 can be provided with a temperature sensor. When the temperature of the filter material rises, this usually means that a reaction takes place, which means that the filter material becomes saturated there. When the transponder 41 with the temperature sensor is arranged near the downstream end of the filter housing 10, it can thus be determined whether the filter is about to leak. Then the transponder 41 thus serves as an indicator and the housing of the filter no longer needs to be designed transparently and can be manufactured from, for instance, metal.

The transponder 41 can also be used for storing the historical field data of the quick-change filter 2 in question. In this manner, service life, flow measurements and/or temperature measurements can be stored in the memory of the transponder 41. Such data can simply be used to deduce a remaining life.

Figure 7:
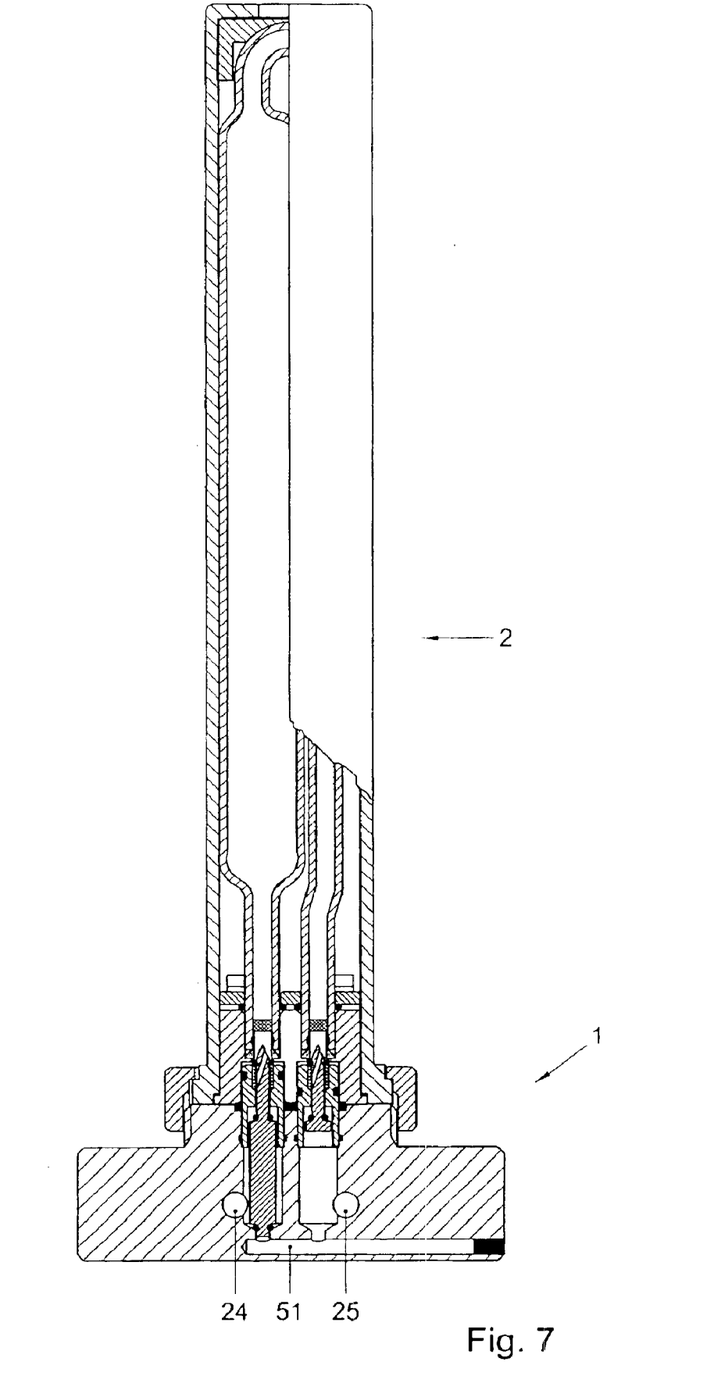
FIG. 7 shows a cross-sectional view of a third alternative embodiment of a base with a filter placed thereon.
Figure 8:
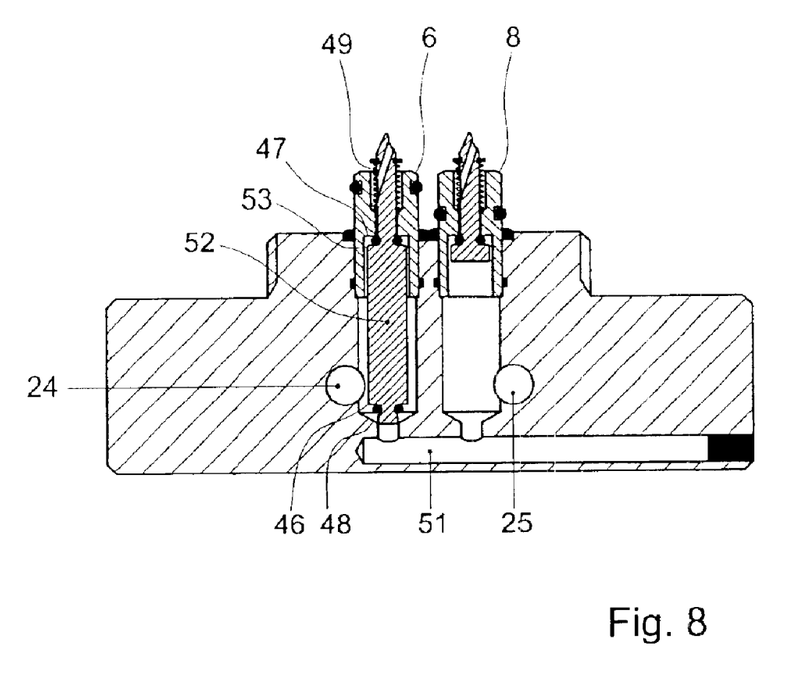
FIG. 8 shows the base of FIG. 7 without a filter placed thereon.

What is special about FIG. 7 is that the base 1 is provided with a by-pass pipe 51 and with means for creating a fluid connection between the inlet connecting element 3 and the outlet connecting element 4 via the by-pass pipe 51 when a quick-change filter 2 is decoupled from the base 1 and for closing off this fluid connection when a quick-change filter 2 is placed on the base 1. In the present exemplary embodiment, the means are formed by incorporating in the gas inlet stub 6 a pin 52 which is longitudinally adjustable in relation to the base 1, which pin is provided with a first and second sealing face 53, 46. The base 1, more in particular the gas inlet stub 6 thereof, contains a first and second valve seat 47, 48. In a first position, the pin 52 lies with the first sealing face 53 against the first valve seat 47 and thus forms a block in a fluid connection between the gas inlet stub 6 and the inlet connecting element 3 while a fluid connection is present between the inlet connecting element 3 and the by-pass pipe 51 (see FIG. 8). In a second position, the pin lies with the second sealing face 46 against the second valve seat 48 and thus forms a block in a fluid connection between the by-pass pipe 51 and the inlet connecting element 3 while a fluid connection is present between gas inlet stub 6 and the inlet connecting element 3 (see FIG. 7). The pin 52 is pressed into the position shown in FIG. 8 by a spring 49. Due to the presence of the by-pass pipe 51, the pipe system as well as the base 1 remain filled with carrier gas and thus the underlying process, such as for example gas chromatography, mass spectrography or LCMS can continue. Admittedly, unfiltered gas is briefly used, but this generally presents no problem to the underlying process. In any case, the duration of the flushing after changing the filter can be considerably reduced or omitted completely.

Figure 9:
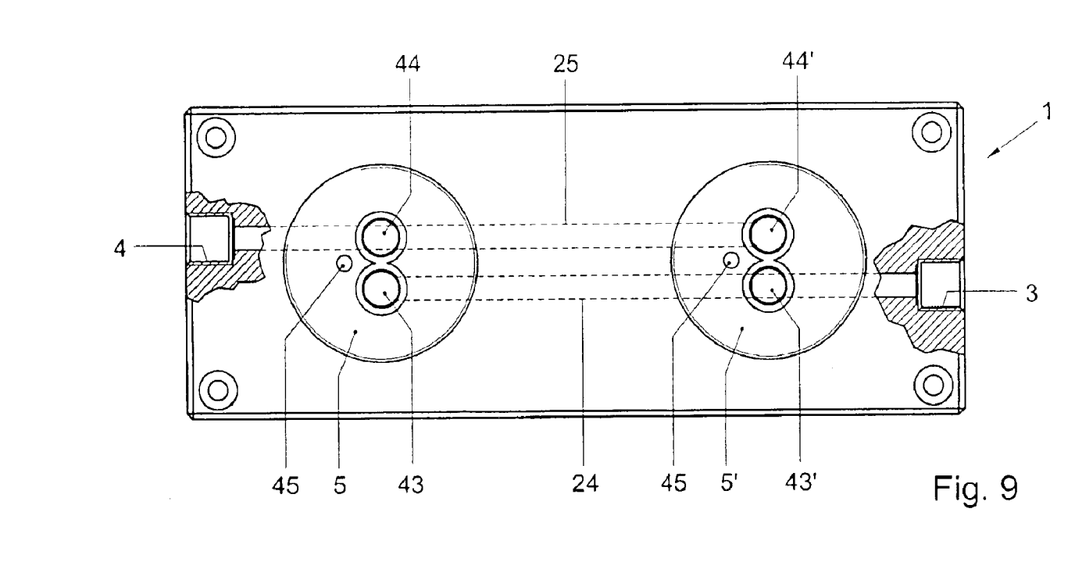
FIGS. 9–11 show a top, front and right side view respectively of a base with two filter coupling parts, omitting the gas inlet and gas outlet stubs.
Figure 10:
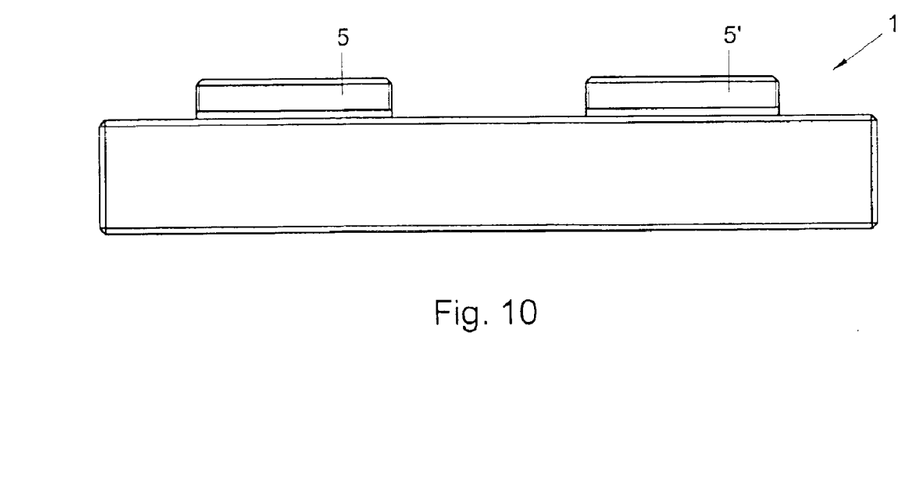
Figure 11:
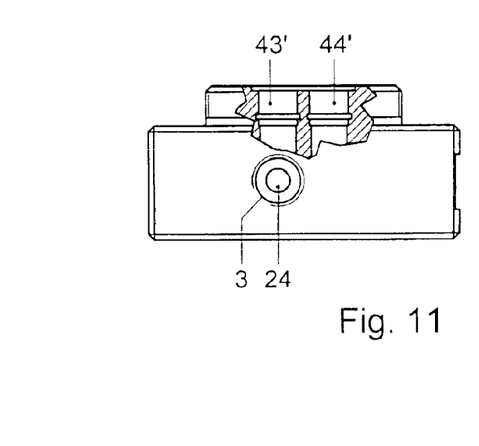

FIGS. 9–11 show a top, front and right side view respectively of a base 1 provided with a pair of filter coupling parts 5. In FIGS. 9–11, the gas inlet stubs and the gas outlet stubs are not shown. FIGS. 9–11 do show the openings 43, 44 in which the gas inlet and gas outlet stubs are to be fitted. Also, openings are shown in which a dowel pin is incorporated in the completed condition of the base 1. The gas inlet and gas outlet stubs as well as the dowel pins 50, 50' are visible, however, in the cross-sectional views of FIGS. 12 and 13. On such a base, two quick-change filters 2 of the same type can be placed. The base is embodied such that the quick-change filters 2 are then connected in parallel in the pipe system. For this purpose, the inlet connecting element 3 connects to an inlet channel 24 in the base. The outlet connecting element 4 connects to an outlet channel 25 in the base. The gas inlet stubs 6, 6' of a pair of filter coupling parts 5, 5' each are connected to the inlet channel 24. The gas outlet stubs such as the gas outlet stub 8 of a pair of filter coupling parts 5, 5' each are connected to the outlet channel 25. The gas flowing into the inlet channel 24 will thus spread over the two filters 2 and after flowing through the filters, which takes place at low speed, so that, surprisingly, not only a longer standing time of the filters is obtained, but also a better cleaning, will leave the base 1 via the outlet channel 25. In particular for processes which require a large gas flow, such as for example an LCMS process, such a parallel connection is a great advantage.

Figure 12:
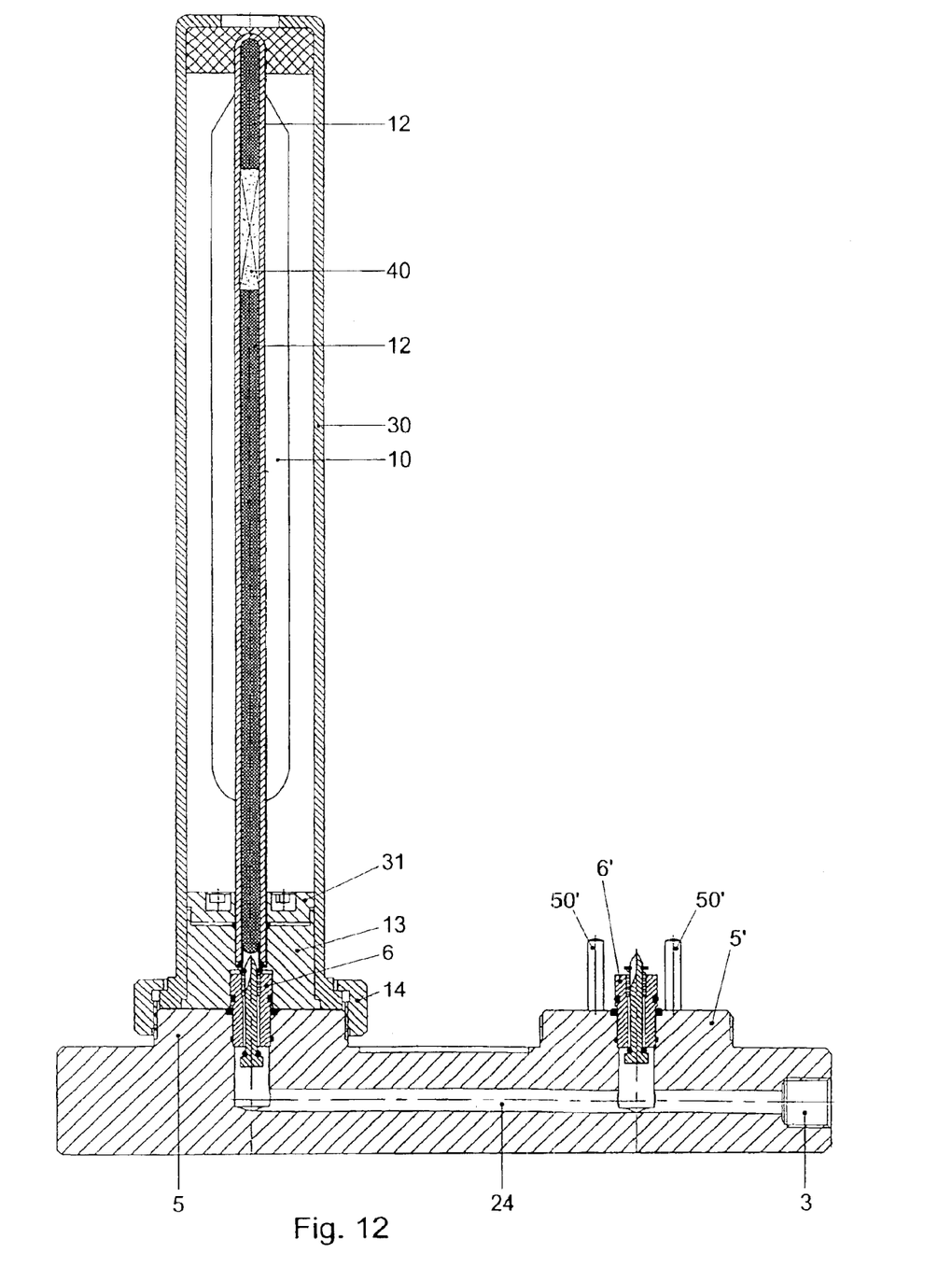
FIG. 12 shows a cross-sectional view of the base shown in FIG. 9 with gas inlet and gas outlet stubs and with a filter placed thereon.
Figure 13:
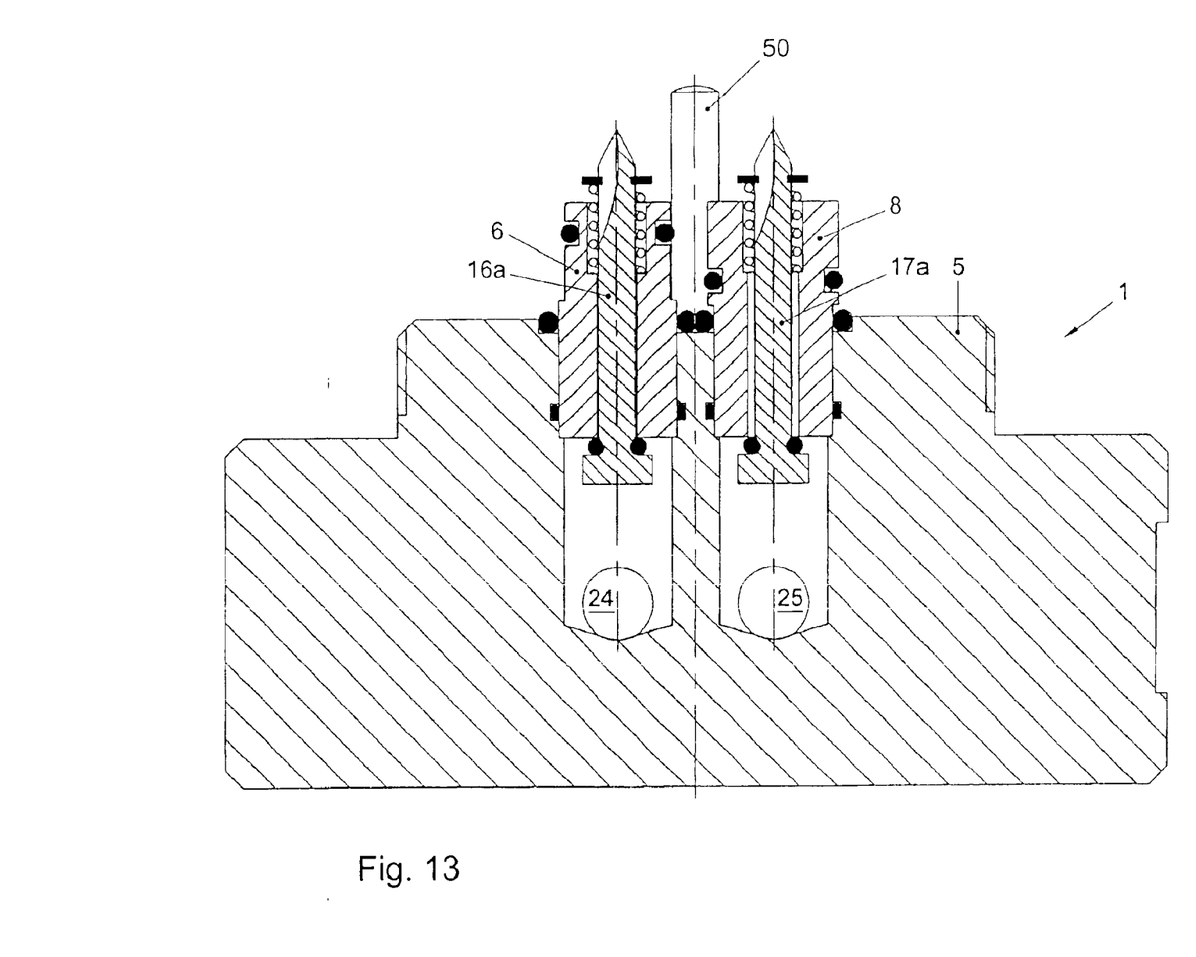
FIG. 13 shows, in more detail, the gas inlet and gas-outlet stub of the exemplary embodiment shown in FIG. 12.

In FIG. 13, a number of other details of the base 1 shown in FIG. 12 are shown. Incidentally, these details can be applied equally fruitfully in a single base. Firstly, it is clearly visible in this figure that the flow room in the gas inlet stub 6 around the valve stem 16a is considerably smaller than the flow room in the gas outlet stub 8 around the valve stem 17a. This makes the flow resistance in the gas inlet stub 6 considerably larger than the flow resistance in the gas outlet stub 8. As a result thereof, the chance of stagnation or backflow of gas within the filter housing 10 is minimized, which has a favorable influence on the cleaning effect of the filter 2. In order to achieve this, in the present exemplary embodiment both the inside diameter and the outside diameter of the gas outlet stub 8 are designed larger than those of gas inlet stub 6. These diameter differences do not only prevent backflow in the filter, but also have the particularly favorable additional advantage that, even without the presence of dowel pins 50, wrong mounting of a filter 2 on the base is prevented The gas stubs 6, 8 with the different diameters thus form a unique form feature. This form feature also ensures that filters of other manufacturers do not fit to a thus designed base. In this manner, the good effect of the quick-change filter system can be better guaranteed. In fact, all parts will be coming from one manufacturer. Optionally, further form features can be added to the base 1. For instance, the gas inlet stub 6 can have a greater length, at least extend further out of the filter coupling part 5 than the gas outlet stub 8. Also, it is possible to provide more than one dowel pin 50, which is shown in FIG. 12. The presence of more than one dowel pin provides a solid and stable connection between the quick-change filter 2 and the base 1. Furthermore, the dowel pin could have such a length that it completely extends through the quick-change coupling 13 and the clamping plate 31 of the quick-change filter 2. This makes the connection of filters provided with a cylindrical housing completely filled with filter material impossible. Such filters are put into circulation by, for instance, Varian Chrompack.

It will be clear that the invention is not limited to the exemplary embodiments described, but that various modifications are possible within the scope of the invention as defined in the claims.

The filter housing can, for instance, be manufactured from metal when no indicator to be visually inspected is present in the filter housing.

What is claimed is:

1. A quick-change filter system comprising:
   at least one base and at least one quick-change filter, which base is provided with an inlet connecting element and an outlet connecting element for connecting the base to a fluid pipe system, wherein the base is provided with a filter coupling part provided with a gas inlet stub for connection to an inlet of the quick-change filter and with a gas outlet stub for connection to an outlet of the quick-change filter, wherein the quick-change filter is provided with a filter housing, which is at least partly filled with filter material and to which the inlet and the outlet are connected, and with a quick-change coupling arranged for cooperation with the filter coupling part of the base, wherein the quick-change coupling contains the inlet and the outlet of the quick-change filter, wherein the base is provided with means for manually connecting the quick-change filter to the base, and is provided with sealing means for automatic, gastight sealing of the gas outlet stub and the gas inlet stub when decoupling the quick-change filter from the base,
   wherein the base is also provided with a by-pass pipe and with means for creating a fluid connection between the inlet connecting element and the outlet connecting element via the by-pass pipe when a quick-change filter is decoupled from the base and for closing off this fluid connection when a quick-change filter is placed on the base,
   wherein the means for creating and for closing off a fluid connection comprises a pin which is longitudinally adjustable in relation to the base, which pin is provided with a first and a second sealing face, wherein the base contains a first and a second valve seat, wherein, in a first position, the pin lies with the first sealing face against the first valve seat and thus forms a block in a fluid connection between the gas inlet stub and the inlet connecting element while a fluid connection is present between the inlet connecting element and the by-pass pipe, wherein, in a second position, the pin lies with the second sealing face against the second valve seat and thus forms a block in a fluid connection between the by-pass pipe and the inlet connecting element while a fluid connection is present between the gas inlet stub and the inlet connecting element, and
   wherein the flow resistance of the gas inlet stub is larger than the flow resistance of the gas outlet stub, such that backflow of gas in the filter housing is prevented.

2. The quick-change filter system according to claim 1, wherein the diameter of the gas inlet stub is smaller than that of the gas outlet stub.

3. The quick-change filter system according to claim 2, wherein both the inside diameter and the outside diameter of the gas inlet stub are smaller than the respective inside diameter and outside diameter of the gas outlet stub.

4. The quick-change filter system according to claim 1, wherein both the inside diameter and the outside diameter of the gas inlet stub are smaller than the respective inside diameter and outside diameter of the gas outlet stub.

5. A quick-change filter system comprising:
   at least one base and at least one quick-change filter, which base is provided with an inlet connecting element and an outlet connecting element for connecting the base to a fluid pipe system, wherein the base is provided with a filter coupling part provided with a gas inlet stub for connection to an inlet of the quick-change filter and with a gas outlet stub for connection to an outlet of the quick-change filter, wherein the quick-change filter is provided with a filter housing, which is at least partly filled with filter material and to which the inlet and the outlet are connected, and with a quick-change coupling arranged for cooperation with the filter coupling part of the base, wherein the quick-change coupling contains the inlet and the outlet of the quick-change filter, wherein the base is provided with means for manually connecting the quick-change filter to the base, and is provided with sealing means for automatic, gastight sealing of the gas outlet stub and the gas inlet stub when decoupling the quick-change filter from the base,
   wherein the base is also provided with a by-pass pipe and with means for creating a fluid connection between the inlet connecting element and the outlet connecting element via the by-pass pipe when a quick-change filter is decoupled from the base and for closing off this fluid connection when a quick-change filter is placed on the base,
   wherein the means for creating and for closing off a fluid connection comprises a pin which is longitudinally adjustable in relation to the base, which pin is provided with a first and a second sealing face, wherein the base contains a first and a second valve seat, wherein, in a first position, the pin lies with the first sealing face against the first valve seat and thus forms a block in a fluid connection between the gas inlet stub and the inlet connecting element while a fluid connection is present between the inlet connecting element and the by-pass pipe, wherein, in a second position, the pin lies with the second sealing face against the second valve seat and thus forms a block in a fluid connection between the by-pass pipe and the inlet connecting element while a fluid connection is present between the gas inlet stub and the inlet connecting element, and
   wherein the filter housing is manufactured from glass, so that it is transparent, wherein the housing contains, in addition to the filter material, an indicator that changes color when the filter material is saturated or at least loses its filtering effect, wherein the filter material removes hydrocarbons from the gas, wherein the indicator changes color when it comes into contact with hydrocarbons.

6. The quick-change filter system according to claim 5, wherein the indicator contains potassium dichromate.

7. The quick-change filter system according to claim 6, wherein the filter material comprises active carbon.

8. A The quick-change filter system according to claim 5, wherein the filter material comprises active carbon.

9. A quick-change filter system comprising:

at least one base and at least one quick-change filter, which base is provided with an inlet connecting element and an outlet connecting element for connecting the base to a fluid pipe system, wherein the base is provided with a filter coupling part provided with a gas inlet stub for connection to an inlet of the quick-change filter and with a gas outlet stub for connection to an outlet of the quick-change filter, wherein the quick-change filter is provided with a filter housing, which is at least partly filled with filter material and to which the inlet and the outlet are connected, and with a quick change coupling arranged for cooperation with the filter coupling part of the base, wherein the quick-change coupling contains the inlet and the outlet of the quick-change filter, wherein the base is provided with means for manually connecting the quick-change filter to the base, and is provided with sealing means for automatic, gastight sealing of the gas outlet stub and the gas inlet stub when decoupling the quick-change filter from the base, wherein the base is also provided with a by-pass pipe and with means for creating a fluid connection between the inlet connecting element and the outlet connecting element via the by-pass pipe when a quick-change filter is decoupled from the base and for closing off this fluid connection when a quick-change filter is placed on the base, wherein the means for creating and for closing off a fluid connection comprises a pin which is longitudinally adjustable in relation to the base, which pin is provided with a first and a second sealing face, wherein the base contains a first and a second valve seat, wherein, in a first position, the pin lies with the first sealing face against the first valve seat and thus forms a block in a fluid connection between the gas inlet stub and the inlet connecting element while a fluid connection is present between the inlet connecting element and the by-pass pipe, wherein, in a second position, the pin lies with the second sealing face against the second valve seat and thus forms a block in a fluid connection between the by-pass pipe and the inlet connecting element while a fluid connection is present between the gas inlet stub and the inlet connecting element, and wherein in the quick-change filter system, two quick-change filters of the same type are connected in parallel in the pipe system.

10. The quick-change filter system according to claim 9, wherein the quick-change filter system contains a base that is provided with at least one pair of filter coupling parts, wherein the inlet connecting element connects to an inlet channel in the base, wherein the outlet connecting element connects to an outlet channel in the base, wherein the gas inlet stubs of a pair of filter coupling parts are each connected to the inlet channel, wherein the gas outlet stubs of a pair of filter coupling parts are each connected to the outlet channel.

11. A quick-change filter system comprising:

at least one base and at least one quick-change filter, which base is provided with an inlet connecting element and an outlet connecting element for connecting the base to a fluid pipe system, wherein the base is provided with a filter coupling part provided with a gas inlet stub for connection to an inlet of the quick-change filter and with a gas outlet stub for connection to an outlet of the quick-change filter, wherein the quick-change filter is provided with a filter housing, which is at least partly filled with filter material and to which the inlet and the outlet are connected, and with a quick-change coupling arranged for cooperation with the filter coupling part of the base, wherein the quick-change coupling contains the inlet and the outlet of the quick-change filter, wherein the base is provided with means for manually connecting the quick-change filter to the base, and is provided with sealing means for automatic, gastight sealing of the gas outlet stub and the gas inlet stub when decoupling the quick-change filter from the base, wherein the base is also provided with a by-pass pipe and with means for creating a fluid connection between the inlet connecting element and the outlet connecting element via the by-pass pipe when a quick-change filter is decoupled from the base and for closing off this fluid connection when a quick-change filter is placed on the base, wherein the means for creating and for closing off a fluid connection comprises a pin which is longitudinally adjustable in relation to the base, which pin is provided with a first and a second sealing face, wherein the base contains a first and a second valve seat, wherein, in a first position, the pin lies with the first sealing face against the first valve seat and thus forms a block in a fluid connection between the gas inlet stub and the inlet connecting element while a fluid connection is present between the inlet connecting element and the by-pass pipe, wherein, in a second position, the pin lies with the second sealing face against the second valve seat and thus forms a block in a fluid connection between the by-pass pipe and the inlet connecting element while a fluid connection is present between the gas inlet stub and the inlet connecting element, and wherein in a quick-change filter thereof a transponder is incorporated.

12. The quick-change filter system according to claim 11, wherein a base thereof is provided with a receiver for reading out a transponder of a quick-change filter.

13. The quick-change filter system according to claim 12, wherein the transponder is provided with a temperature sensor.

14. The quick-change filter system according to claim 11, wherein the transponder is provided with a temperature sensor.

15. A quick-change filter system comprising: at least one base and at least one quick-change filter, which base is provided with an inlet connecting element and an outlet connecting element for connecting the base to a fluid pipe system, wherein the base is provided with a filter coupling part provided with a gas inlet stub for connection to an inlet of the quick-change filter and with a gas outlet stub for connection to an outlet of the quick-change filter, wherein the quick-change filter is provided with a filter housing, which is at least partly filled with filter material and to which the inlet and the outlet are connected, and with a quick-change coupling arranged for cooperation with the filter coupling part of the base, wherein the quick-change coupling contains the inlet and the outlet of the quick-change filter, wherein the base is provided with means for manually connecting the quick-change filter to the base, and is provided with sealing means for automatic, gastight sealing of the gas outlet stub and the gas inlet stub when decoupling the quick-change filter from the base, wherein the base is also provided with a by-pass pipe and with means for creating a fluid connection between the inlet connecting element and the outlet connecting element via the by-pass pipe when a quick-change filter is decoupled from the base and for closing off this fluid connection when a quick-change filter is placed on the base, wherein the means for creating and for closing off a fluid connection comprises a pin which is longitudinally adjustable in relation to the base, which pin is provided with a first and a second sealing face, wherein the base contains a first and a second valve seat, wherein, in a first position, the pin lies with the first sealing face against the first valve seat and thus forms a block in a fluid connection between the gas inlet stub and the inlet connecting element while a fluid connection is present between the inlet connecting element and the by-pass pipe, wherein, in a second position, the pin lies with the second sealing face against the second valve seat and thus forms a block in a fluid connection between the by-pass pipe and the inlet connecting element while a fluid connection is present between the gas inlet stub and the inlet connecting element.

16. A quick-change filter system comprising:
at least one base and at least one quick-change filter, which base is provided with an inlet connecting element and an outlet connecting element for connecting the base to a fluid pipe system, wherein the base is provided with a filter coupling part provided with a gas inlet stub for connection to an inlet of the quick-change filter and with a gas outlet stub for connection to an outlet of the quick-change filter, wherein the quick-change filter is provided with a filter housing, which is at least partly filled with filter material and to which the inlet and the outlet are connected, and with a quick-change coupling arranged for cooperation with the filter coupling part of the base, wherein the quick-change coupling contains the inlet and the outlet of the quick-change filter, wherein the base is provided with means for manually connecting the quick-change filter to the base, and is provided with sealing means for automatic, gastight sealing of the gas outlet stub and the gas inlet stub when decoupling the quick-change filter from the base,
wherein the base is also provided with a by-pass pipe and with means for creating a fluid connection between the inlet connecting element and the outlet connecting element via the by-pass pipe when a quick-change filter is decoupled from the base and for closing off this fluid connection when a quick-change filter is placed on the base,
wherein the means for creating and for closing off a fluid connection comprises a pin which is longitudinally adjustable in relation to the base, which pin is provided with a first and a second sealing face, wherein the base contains a first and a second valve seat, wherein, in a first position, the pin lies with the first sealing face against the first valve seat and thus forms a block in a fluid connection between the gas inlet stub and the inlet connecting element while a fluid connection is present between the inlet connecting element and the by-pass pipe, wherein, in a second position, the pin lies with the second sealing face against the second valve seat and thus forms a block in a fluid connection between the by-pass pipe and the inlet connecting element while a fluid connection is present between the gas inlet stub and the inlet connecting element, and
wherein the filter coupling part of the base and the quick coupling of the quick-change filter are provided with mutually cooperating form features, which ensure that only quick-change filters intended for the base in question can be placed on the base.

17. The quick-change filter system according to claim 16, wherein the form features concern the diameters of the gas inlet stub and the gas outlet stub.

18. The quick-change filter system according to claim 17, wherein the inside diameter of the gas inlet stub is smaller than the inside diameter of the gas outlet stub.

19. The quick-change filter system according to claim 18, wherein the outside diameter of the gas inlet stub is smaller than the outside diameter of the gas outlet stub.

20. The quick-change filter system according to claim 17, wherein the outside diameter of the gas inlet stub is smaller than the outside diameter of the gas outlet stub.

21. The quick-change filter system according to claim 16, wherein the form features concern the lengths of the gas inlet stub and the gas outlet stub.

22. The quick-change filter system according to claim 16, wherein the form features comprise at least one dowel pin on the filter coupling part of the base.

23. The quick-change filter system according to claim 22, wherein more than one dowel pin is provided on the filter coupling part of the base.

24. The quick-change filter system according to claim 23, wherein the length of at least one dowel pin is such that this pin, in mounted condition of the quick-change filter on the base, completely extends through the quick-change coupling of the filter, wherein a bore through the quick-change coupling is provided.

25. The quick-change filter system according to claim 22, wherein the length of at least one dowel pin is such that this pin, in mounted condition of the quick-change filter on the base, completely extends through the quick-change coupling of the filter, wherein a bore through the quick-change coupling is provided.

26. A quick-change filter system comprising:
at least one base and at least one quick-change filter, which base is provided with an inlet connecting element and an outlet connecting element for connecting the base to a fluid pipe system, wherein the base is provided with a filter coupling part provided with a gas inlet stub for connection to an inlet of the quick-change filter and with a gas outlet stub for connection to an outlet of the quick-change filter, wherein the quick-change filter is provided with a filter housing, which is at least partly filled with filter material and to which the inlet and the outlet are connected, and with a quick-change coupling arranged for cooperation with the filter coupling part of the base, wherein the quick-change coupling contains the inlet and the outlet of the quick-change filter, wherein the base is provided with means for manually connecting the quick-change filter to the base, and is provided with sealing means for automatic, gastight sealing of the gas outlet stub and the gas inlet stub when decoupling the quick-change filter from the base,
wherein the base is also provided with a by-pass pipe and with means for creating a fluid connection between the inlet connecting element and the outlet connecting element via the by-pass pipe when a quick-change filter is decoupled from the base and for closing off this fluid connection when a quick-change filter is placed on the base,
wherein the means for creating and for closing of if a fluid connection comprises a pin which is longitudinally adjustable in relation to the base, which pin is provided with a first and a second sealing face, wherein the base contains a first and a second valve seat, wherein, in a first position, the pin lies with the first sealing face against the first valve seat and thus forms a block in a fluid connection between the gas inlet stub and the inlet connecting element while a fluid connection is present between the inlet connecting element and the by-pass pipe, wherein, in a second position, the pin lies with the second sealing face against the second valve seat and thus forms a block in a fluid connection between the by-pass pipe and the inlet connecting element while a fluid connection is present between the gas inlet stub and the inlet connecting element, and wherein a quick-change filter from the system has already been pre-flushed in the factory, using the gas that will later clean the system, wherein after pre-flushing, the filter housing is constructed and sealed such that hardly any air or gasses from the air diffuse into the filter or flushing gas diffuses out of the filter.

27. A quick-change filter intended for use in a filter system, the filter system comprising:

at least one base, which base is provided with an inlet connecting element and an outlet connecting element for connecting the base to a fluid pipe system, wherein the base is provided with a filter coupling part provided with a gas inlet stub for connection to an inlet of the quick-change filter and with a gas outlet stub for connection to an outlet of the quick-change filter, wherein the quick-change filter is provided with a filter housing, which is at least partly filled with filter material and to which the inlet and the outlet are connected, and with a quick-change coupling arranged for cooperation with the filter coupling part of the base, wherein the quick-change coupling contains the inlet and the outlet of the quick-change filter, wherein the base is provided with means for manually connecting the quick-change filter to the base, and is provided with sealing means for automatic, gastight sealing of the gas outlet stub and the gas inlet stub when decoupling the quick-change filter from the base, wherein the base is also provided with a by-pass pipe and with means for creating a fluid connection between the inlet connecting element and the outlet connecting element via the by-pass pipe when a quick-change filter is decoupled from the base and for closing off this fluid connection when a quick-change filter is placed on the base, wherein the means for creating and for closing off a fluid connection comprises a pin which is longitudinally adjustable in relation to the base, which pin is provided with a first and a second sealing face, wherein the base contains a first and a second valve seat, wherein, in a first position, the pin lies with the first sealing face against the first valve seat and thus forms a block in a fluid connection between the gas inlet stub and the inlet connecting element while a fluid connection is present between the inlet connecting element and the by-pass pipe, wherein, in a second position, the pin lies with the second sealing face against the second valve seat and thus forms a block in a fluid connection between the by-pass pipe and the inlet connecting element while a fluid connection is present between the gas inlet stub and the inlet connecting element, and wherein the flow resistance of the gas inlet stub is larger than the flow resistance of the gas outlet stub, such that back flow of gas in the filter housing is prevented.

28. A base intended for use in a filter system, the filter system comprising:

at least one quick-change filter, wherein the base is provided with an inlet connecting element and an outlet connecting element for connecting the base to a fluid pipe system, wherein the base is provided with a filter coupling part provided with a gas inlet stub for connection to an inlet of the quick-change filter and with a gas outlet stub for connection to an outlet of the quick-change filter, wherein the quick-change filter is provided with a filter housing, which is at least partly filled with filter material and to which the inlet and the outlet are connected, and with a quick-change coupling arranged for cooperation with the filter coupling part of the base, wherein the quick-change coupling contains the inlet and the outlet of the quick-change filter, wherein the base is provided with means for manually connecting the quick-change filter to the base, and is provided with sealing means for automatic, gastight sealing of the gas outlet stub and the gas inlet stub when decoupling the quick-change filter from the base, wherein the base is also provided with a by-pass pipe and with means for creating a fluid connection between the inlet connecting element and the outlet connecting element via the by-pass pipe when a quick-change filter is decoupled from the base and for closing off this fluid connection when a quick-change filter is placed on the base, wherein the means for creating and for closing off a fluid connection comprises a pin which is longitudinally adjustable in relation to the base, which pin is provided with a first and a second sealing face, wherein the base contains a first and a second valve seat, wherein, in a first position, the pin lies with the first sealing face against the first valve seat and thus forms a block in a fluid connection between the gas inlet stub and the inlet connecting element while a fluid connection is present between the inlet connecting element and the by-pass pipe, wherein, in a second position, the pin lies with the second sealing face against the second valve seat and thus forms a block in a fluid connection between the by-pass pipe and the inlet connecting element while a fluid connection is present between the gas inlet stub and the inlet connecting element, and wherein the flow resistance of the gas inlet stub is larger than the flow resistance of the gas outlet stub, such that backflow of gas in the filter housing is prevented.

* * * * *

UNITED STATES PATENT AND TRADEMARK OFFICE
CERTIFICATE OF CORRECTION

PATENT NO. : 6,918,952 B2 Page 1 of 1
APPLICATION NO. : 10/449817
DATED : July 19, 2005
INVENTOR(S) : Marinus Frans van der Maas

It is certified that error appears in the above-identified patent and that said Letters Patent is hereby corrected as shown below:

Column 12, line 62, "of if" should read --off--; and

Column 14, line 7, "back flow" should read --backflow--.

Signed and Sealed this

Twenty-second Day of August, 2006

JON W. DUDAS
*Director of the United States Patent and Trademark Office*